(12) United States Patent
Jia et al.

(10) Patent No.: US 7,275,933 B2
(45) Date of Patent: *Oct. 2, 2007

(54) METHOD OF MANUFACTURING DENTAL RESTORATIONS

(75) Inventors: Weitao Jia, Wallingford, CT (US); Shuhua Jin, Wallingford, CT (US)

(73) Assignee: Pentron Clinical Technologies, LLC, Wallingford, CT (US)

(*) Notice: Subject to any disclaimer, the term of this patent is extended or adjusted under 35 U.S.C. 154(b) by 317 days.

This patent is subject to a terminal disclaimer.

(21) Appl. No.: 10/862,177

(22) Filed: Jun. 4, 2004

(65) Prior Publication Data

US 2004/0249015 A1 Dec. 9, 2004

Related U.S. Application Data

(60) Division of application No. 10/005,298, filed on Dec. 5, 2001, now Pat. No. 6,787,584, which is a continuation-in-part of application No. 09/638,206, filed on Aug. 11, 2000, now Pat. No. 6,455,608.

(60) Provisional application No. 60/251,408, filed on Dec. 5, 2000.

(51) Int. Cl.
*A61C 5/04* (2006.01)
*A61K 6/08* (2006.01)

(52) U.S. Cl. .................. 433/228.1; 523/115; 523/116; 523/117

(58) Field of Classification Search ................. 523/115; 433/228.1
See application file for complete search history.

(56) References Cited

U.S. PATENT DOCUMENTS

| | | | |
|---|---|---|---|
| 3,066,112 A | 11/1962 | Bowen | |
| 3,925,895 A | 12/1975 | Kliment et al. | |
| 3,991,008 A | 11/1976 | Temin et al. | |
| 4,103,002 A | 7/1978 | Hench et al. | |
| 4,159,358 A | 6/1979 | Hench et al. | |
| 4,171,544 A | 10/1979 | Hench et al. | |
| 4,189,325 A | 2/1980 | Barrett et al. | |
| 4,234,972 A | 11/1980 | Hench et al. | |
| 4,240,832 A | 12/1980 | Jandourek | |
| 4,343,608 A | 8/1982 | Hodosh | |
| 4,407,675 A | 10/1983 | Hodosh | |
| 4,449,938 A | 5/1984 | Pollak | |
| 4,544,359 A | 10/1985 | Waknine | |
| 4,547,531 A | 10/1985 | Waknine | |
| 4,657,592 A | 4/1987 | Takubo | |
| 4,732,943 A | 3/1988 | Beech et al. | |
| 4,775,646 A | 10/1988 | Hench et al. | |
| 4,851,046 A | 7/1989 | Low et al. | |
| 4,931,096 A | 6/1990 | Fujisawa | |
| 4,986,754 A | 1/1991 | Chang et al. | |
| 5,074,916 A | 12/1991 | Hench et al. | |
| 5,236,362 A | 8/1993 | Cohen et al. | |
| 5,380,772 A | 1/1995 | Hasegawa et al. | |
| 5,518,680 A | 5/1996 | Cima et al. | |
| 5,542,973 A | 8/1996 | Chow et al. | |
| 5,624,976 A | 4/1997 | Klee | |
| 5,735,942 A | 4/1998 | Litkowski et al. | |
| 5,837,752 A | 11/1998 | Shastri et al. | |
| 5,891,233 A | 4/1999 | Salonen et al. | |
| 5,900,245 A | 5/1999 | Sawhney et al. | |
| 5,915,970 A | 6/1999 | Sicurelli, Jr. et al. | |
| 5,981,412 A | 11/1999 | Hench et al. | |
| 6,013,591 A | 1/2000 | Ying et al. | |
| 6,051,247 A | 4/2000 | Hench et al. | |
| 6,054,400 A | 4/2000 | Brink et al. | |
| 6,086,374 A | 7/2000 | Litkowski et al. | |
| 6,455,608 B1 | 9/2002 | Jia et al. | |

FOREIGN PATENT DOCUMENTS

| | | |
|---|---|---|
| EP | 0 438 255 A2 | 7/1991 |
| JP | 5163480 | 6/1993 |
| WO | WO 96/19179 | 6/1996 |
| WO | WO 98/20839 | 5/1998 |
| WO | WO 01/12129 A1 | 2/2001 |
| WO | WO 02/078646 A1 | 10/2002 |

OTHER PUBLICATIONS

International Search Report with date of mailing Dec. 5, 2000.
International Search Report with date of mailing Mar. 12, 2002.
Hench, LL, "The Kinetics of Bioactive Ceramics—Part I: Reaction Rates" BIOCERAMICS 3rd Intl Symp Ceramics in Medicine; Terre Haute, IN; Nov. 1990, pp. 43-45.

(Continued)

*Primary Examiner*—Tae H Yoon
(74) *Attorney, Agent, or Firm*—Ann M. Knab

(57) ABSTRACT

Method of manufacturing dental restorations using curable compositions including degradable macromonomers having one or more terminal acrylate or methacrylate functionality, a curing composition, a filler composition including bioactive particles of bioactive glass, bioactive glass-ceramics, calcium phosphates, calcium apatites, or mixtures thereof and optionally one or more polymerizable acrylate or methacrylate comonomers. Degradable macromonomers are manufactured from cyclic monomers with compounds having acrylate or methacrylate functionality. Depending on their use, the degradable macromonomer compositions further include one or more organic or inorganic fillers, including a calcium-based compound and/or a radiopacity-imparting agent. The compositions are particularly suitable for root canal sealants, implants, bone cements, and pulp capping materials.

13 Claims, No Drawings

OTHER PUBLICATIONS

Andersson, OH., "The Kinetics of Bioactive Ceramics—Part II: Surface Reactions of Three Bioactive Glasses" BIOCERAMICS: 3rd Intl Symp Ceramics in Medicine; Terre Haute, IN; Nov. 1990; ISM, pp. 46-end of article.

Hench, LL, Anderson, OH, "The Kinetics of Bioactive Cermaics Part III: Surface Reactions of Bioactive Glasses Compared with Inactive Glass"—BIOCERAMICS, Sep. 1991, pp. 155-162.

Hench, LL., Latorre, GP, "Reaction Kinetics of Bioactive Ceramics Part IV: Effect of Glass and Solution Composition", BIOCERAMICS, vol. 5, pp. 67-74, 1992.

West, JK; Hench, LL, "Reaction Kinetics of Bioactive Ceramics Part V: Molecular Orbital Modelling of Bioactive Glass Surface Reactions" BIOCERAMICS, vol. 5, pp. 75-86, 1992.

Zhong, JP, "The Kinetics of Bioactive Ceramics Part VII: Binding of Collagen to Hydroxyapatite and Bioactive Glass", BIOCERAMICS, vol. 7, Jul. 1994, pp. 61-66.

Onyarl, JM; Huang, SJ; "Multi-Component Comb Shaped and Networks Containing Poly(Lactic Acid)", Polymer Mat. Sci, Eng. 72(1), pp. 137-138 (1995).

Huang, SJ; Onyari, JM; "Multicomponent Polymers of Poly(Lactic Acid)Marcomonomers with Methacrylate Terminal and Copolymers of Poly(2-Hydroxyethyl Methacrylate)", Journal of Macromolecular Science, Pure Applied Chemistry, A33 (5), pp. 571-584 (1996).

Eguiburu, JL; Fernandex Berridi, MJ; San Roman J; "Functionalization of Poly(L-lactide)Macromonomers By Ring-Opening Polymerization of L-lactide Initiated With Hydroxyethyl Methacrylate-Aluminum Alkoxides", Polymer, vol. 36, No. 1 (1995), pp. 173-179.

Barakat, I; Dubois, PH; Jerome, R; Teyssie, PH; Goethals, E; "Macromolecular Engineering of Polyactones and Polyactides XV. Poly(D,L)-lactide Macromonomers as Precursors of Biocompatible Graft Copolymers and Bioerodible Gels", Journal of Polymer Science, Part A, Polymer Chemistry, vol. 32, No. 11, Aug. 1994, pp. 2099-2110.

Eguibure, JL et al.; "Graft Copolymers for Biomedical Applications Prepared by Free Radical Polymerization of Poly(l-lactide)macromonomers with Vinyl and Acrylic Monomers", Polymer, Elsevier Science Publishers BV, GB, vol. 37, No. 16, Aug. 1, 1996, pp. 3615-3622.

Han, YK; Ederman, PG; Huang, SJ; "Synthesis and Characterization of Crosslinked Polymers for Biomedical Composites", Journal of Macromolecular Sci.-Chem., A25(5-7), pp. 847-869 (1988).

PerioGlass Product Information,U.S. Biomaterials Corporation [http://www.tracomservices.com/perioglas/perioglas.htm], Nov. 15, 2000.

Langstaff,Sarah, "Development of a bulk calcium phosphate ceramic capable of supporting osteoclastic resorption" [http://www.phy-server.queensu.ca/wwwhome/assg/sarah.htm], Nov. 2000.

"The Mineral Apatite", [http://www.galleries.com/minerals/phosphat/apatite/apatite.htm] Nov. 29, 2000.

PerioGlas Product Information from U.S. Biomaterials Corporation, Alachua, Florida [http://www.usblomat.com/perioglas.html],Nov. 15, 2000.

Nova Bone Product Information from U.S. Biomaterials Corporation, Alachua, Florida [http://www.usbiomat.com/novabone.html],Nov. 15, 2000.

Bioglass Procut Information from U.S. Biomaterials Corporation, Alachua, Florida [http://www.usbiomat.com/bioglass.html], Nov. 15, 2000.

"Pushing the boundaries of tradition, researchers are the catalysts for change" [http://www.health.ufl.edu/bullets/invent.html], Nov. 15, 2000.

Database WPI, Section Ch, Week 199330, Darwent Publications Ltd., London, GB, (1993).

METHOD OF MANUFACTURING DENTAL RESTORATIONS

CROSS-REFERENCE TO RELATED APPLICATIONS

This application is a divisional of U.S. application Ser. No. 10/005,298 filed Dec. 5, 2001, and U.S. Pat. No. 6,787,584 B1, which is a continuation-in-part application to application Ser. No. 09/638,206 filed Aug. 11, 2000, now U.S. Pat. No. 6,455,608 B1 and claims the benefit of U.S. Provisional Application Ser. No. 60/251,408 filed Dec. 5, 2000, all of which are hereby incorporated by reference.

BACKGROUND OF THE INVENTION

1. Field of the Invention

This invention relates to dental and medical compositions. In particular, this invention relates to dental/medical compositions comprising degradable copolymers which are suitable for use as root canal sealants, root canal filling materials, dental restorative materials, implant materials, bone cements and pulp capping materials.

2. Description of the Related Art

Endodontic therapy for a diseased or otherwise compromised tooth generally involves the dental practitioner accessing the root canal, debriding and disinfecting the root canal to clean and remove all of the soft tissue (the pulp) therein, and then enlarging the canal to remove irregularities or rough surfaces within the canal. A pre-formed "cone" or "point" is then inserted into the canal, and the cone is laterally or vertically condensed into the canal so that the point of the cone terminates at the apex of the canal. A commonly used cone material is gutta percha, which is a thermoplastic rubber. Because of the many irregularities which remain in the surface and shape of the canal even after treatment, it is difficult to achieve a satisfactory seal between the apex of the root canal and the cone without use of a root canal filler or sealant. Numerous sealants have been described, for example swellable hydrophilic acrylates and methacrylates such as 2-hydroxyethyl methacrylate (HEMA), as disclosed in U.S. Pat. No. 3,925,895 to Kliment et al. The monomers are mixed with polymerization initiator immediately prior to use and delivered to the root where polymerization occurs in situ. U.S. Pat. No. 4,986,754 discloses an injectable endodontic filling material comprising a mixture of balata or gutta percha with a liquid plasticizer. U.S. Pat. No. 4,449,938 discloses use of a two-component, room temperature setting organopolysiloxane compositions used for dental impression materials.

Despite these advances, the most commonly used root canal sealants remain compositions comprising a mixture of zinc oxide with eugenol (ZOE), and mixtures comprising calcium hydroxide. ZOE in particular is irritating to some patients, and has low adhesion to the walls of the root canal. Root canal sealants should be non-toxic, non-irritating, radiopaque, and have no or minimal shrinkage. They should also set within a reasonable period of time. They must be biologically compatible with tooth structure, and are preferably inert to moisture and to the pH conditions found in the mouth. Ideal preparations have low viscosity to facilitate insertion into the root canal, and even more preferably, are thixotropic. In the case of overflow of root canal sealant from the apex into the surrounding tissue or structure during a filling process, the overflowed excess should be desirably absorbed by the surrounding body tissue and cause tissue growth and recovery.

In contrast to endodontic procedures, in certain other dental procedures the pulp of the tooth is left intact. Where the pulp is exposed, a "pulp capping" compound is required which will preserve the vitality of the pulp. Pulp capping compounds must also be non-toxic, and cannot result in any irritation to the pulp. Ideal pulp capping compounds also allow for regrowth of the surrounding tissue and dentine. Calcium hydroxide-based pulp capping compounds are therefore common, as described in U.S. Pat. No. 3,047,400, and in U.S. Pat. No. 4,240,832, which discloses use of condensates of alkyl salicylates with aldehydes reacted with calcium hydroxide or calcium oxide. Despite these advances in the art, there remains a need for pulp capping materials which are biocompatible, non-toxic, and which have advantageous handling properties.

Bioactive glass compositions have been proven effective in activating tissue and bone regrowth. Commercially available materials marketed under BioGlass®, PeroGlas™ and NovaBone™ trademarks available from USBiomaterials Corporation, are supplied in the form of particulates. Although these products have been shown to activate growth of tissue, the applications for the products are limited due to the nature of the particulates. The particulates can only be used for certain applications, such as filling-type applications where no near-term stress or pressure is present. U.S. Pat. No. 6,051,247 to Hench et al. is directed to moldable bioactive compositions comprising a bioactive material in combination with a polysaccharide. The compositions are moldable, but do not cure to hardened form. Accordingly, the compositions are not useful as solid-forming materials that provide strength to the area of application. There remains a need to provide bioactive materials for dental and medical applications in compositions that can provide strength and integrity to the area of application.

SUMMARY OF THE INVENTION

The above-discussed and other drawbacks and deficiencies of the prior art are overcome or alleviated by compositions comprising degradable macromonomers having biodegradable segments selected from the group consisting of poly(lactide), poly(glycolide), and poly(caprolactone), together with terminal acrylate or methacrylate functionality, a curing composition, a filler composition comprising bioactive particles of bioactive glass, bioactive glass-ceramics, bioactive calcium phosphates, bioactive calcium apatites, or mixtures thereof, and optionally a co-polymerizable acrylate or methacrylate monomer. Degradable macromonomers are manufactured by the polymerization of cyclic lactide, glycolide, or caprolactone in the presence of a compound having at least one active hydrogen and at least one acrylate or methacrylate functionality. Preferred active hydrogen containing acrylate or methacrylate compounds comprise 2-hydroxyethyl methacrylate, hydroxypolyethyl methacrylate, phenoxy-2-hydroxypropyl methacrylate, and the like. Preferred co-polymerizable acrylate or methacrylate monomers include diluent monomers such as 1,6-hexanediol dimethacrylate, triethylene glycol trimethacrylate and 2-hydroxyethyl methacrylate. Degradable macromonomers can also be manufactured by the esterification of hydroxyl-group(s) terminated macromonomers of the above-mentioned hydroxy acids with acrylic acid, meth acrylic acid and their derivatives. A degradable macromonomer means degradation by means of hydrolysis and/or biodegradation.

The bioactive particles in the filler composition are characterized by their ability to firmly attach to living tissues, to promote tissue growth and to bond chemically with bone. It has been shown that tissue bonds to bioactive glass due to formation of a Si-gel layer on the bioactive particles. Bioactive particles can be made in the form of powder, granules, blocks and plates of different sizes and shapes.

The present compositions are expected to be biocompatible and biodegradable, which advantageously allows for tissue and bone regrowth. The degradable macromonomer/bioactive filler compositions therefore find particular utility as root canal sealants, implant materials, bone cements and as pulp capping compositions. The above-discussed and other features and advantages of the present invention will be appreciated and understood by those skilled in the art from the following detailed description.

DETAILED DESCRIPTION OF THE PREFERRED EMBODIMENTS

The present compositions comprise degradable macromonomers having terminal acrylate or methacrylate groups, a curing agent, a filler comprising bioactive particles and optionally one or more co-polymerizable acrylate or methacrylate monomer. The degradable macromonomer compositions may further comprise additional organic or inorganic fillers and a radiopacity-imparting agent.

Degradable macromonomers having terminal acrylate or methacrylate groups are obtained by the polymerization and copolymerization of lactide, glycolide or caprolactone in the presence of a compound having at least one active hydrogen, such as an amine or a hydroxyl group, and at least one acrylate or methacrylate functionality. Such compounds include but are not limited to hydroxyalkyl acrylates and methacrylates wherein the alkyl group has from 1 to 12 carbons, such as 2-hydroxyethyl methacrylate (HEMA), 2-hydroxyethyl acrylate, diethylene glycol monomethacrylate, diethylene glycol monoacrylate, hydroxypropyl methacrylate, hydroxypropyl acrylate, tetraethyleneglycol monomethacrylate, tetraethyleneglycol monoacrylate, pentaethyleneglycol monomethacrylate, pentaethyleneglycol monoacrylate, dipropyleneglycol monomethacrylate, dipropyleneglycol monoacrylate, hydroxy polyethyl methacrylates, phenoxyhydroxyphenyl methacrylate and the like. HEMA is preferred. Degradable macromonomers having terminal acrylate or methacrylate groups can also be manufactured by the esterification of hydroxyl-group(s) terminated macromonomers of the above mentioned hydroxy acids with acrylic acid, methacrylic acid and their derivatives.

Lactide is the cyclic dimer of lactic acid, and is available as both L-lactide ((3S)-cis-3,6-dimethyl-1,4-dioxane-2,5-dione) and D,L-lactide (3,6-dimethyl-1,4-dioxane-2,5-dione). Polymerization of lactide with HEMA, for example, yields a poly(lactide-HEMA) (hereinafter PLAMA) macromonomer having the following structure (I), wherein $m=1$, $n \geq 1$, and G is hydroxyl, or acrylate or methacrylate containing terminal non-polymerizable esters:

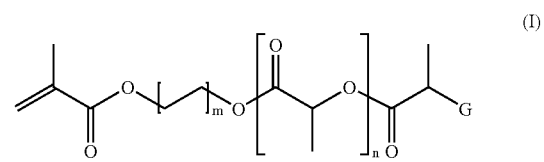

Synthesis of suitable poly(lactic acid) macromonomers having terminal acrylate or methacrylate groups is described by S. J. Huang and J. M. Onyari, in "Multicomponent Polymers of Poly(Lactic) Acid Macromonomers With Methacrylate Terminal and Copolymers of Poly(2-Hydroxyethyl Methacrylate)", in *Journal of Macromolecular Science—Pure and Applied Chemistry*, Volume A33, No. 5, pp. 571-584 (1996); by S. J. Huang and J. M. Onyari in *Polymer Material Science and Engineering*, Volume 72, No. 1, p. 137; by I. Barakat, P. Dubois, R. Jerome, P. Teyssie, and E. Goethais, in *Journal of Polymer Science, Polymer Chem. Ed.*, Vol. 32, p. 2099 (1994); and by J. L. Eguiburu, M. J. F. Berridi, and J. San Romain, *Polymer*, Vol. 36, No. 1, p. 173 (1995). All of the preceding references are incorporated herein in their entirety.

Polymerization of glycolide with HEMA, for example, yields a poly(glycolide-HEMA) macromonomer having the following structure (II), wherein $m=1$, $n \geq 1$, preferably from 5 to 50, and G is hydroxyl, or acrylate or methacrylate containing terminal non-polymerizable esters:

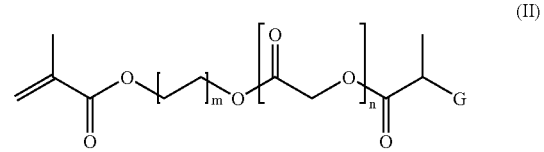

Polymerization of caprolactone with HEMA yields a poly(caprolactone-HEMA) macromonomer having the following structure (III), wherein $m=1$, $n \geq 1$, preferably from 5 to 50, and G is hydroxyl, or acrylate or methacrylate containing terminal non-polymerizable esters:

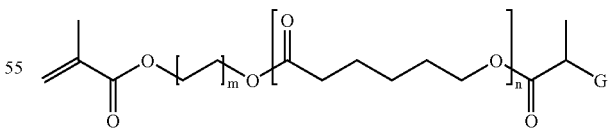

Copolymerization of a mixture of lactide, glycolide, and caprolactone with HEMA yields a macromonomer having the following structure (IV), wherein $m=1$, $n_1$, $n_2$, and $n_3$ are each independently one or greater, preferably from 5 to 50, and G is hydroxyl, or acrylate or methacrylate containing terminal non-polymerizable esters:

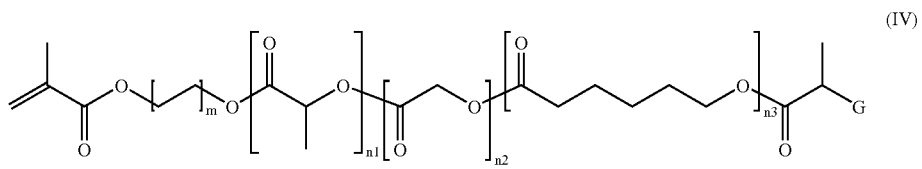

(IV)

Copolymerization of a mixture of lactide and glycolide with HEMA yields PGLMA, a macromonomer having the following structure (V), wherein m=1, $n_1$ and $n_2$ are each independently one or greater, preferably from 5 to 50, and G is hydroxyl, or acrylate or methacrylate containing terminal non-polymerizable esters:

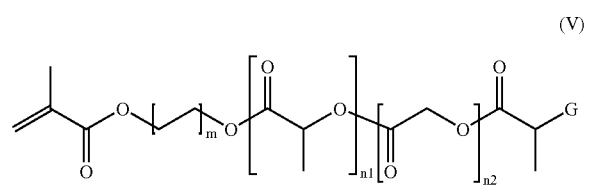

(V)

Another preferred degradable macromonomer is commercially available 2-(caprolactone)ethyl methacrylate (CLMA).

The optional co-polymerizable acrylate or methacrylate monomer is selected from those known for use as dental materials, and is typically present in amounts in the range from 0% to 95% by weight of the total composition. Multi-functional, diluent, i.e., low viscosity monomers, are preferred. Such monomers provide crosslinking and allow the viscosity of the composition to be adjusted for easy delivery to the root canal, while maintaining advantageous physical properties of the polymerized product. Exemplary diluent monomers include but are not limited to liquid dimethacrylate, trimethacrylate, or higher monomers, such as glycerol dimethacrylate, ethylene glycol dimethacrylate, tri(ethylene glycol) dimethacrylate (hereinafter TEGDMA), tetra(methylene glycol) dimethacrylate, trimethylolpropane trimethacrylate, 1,6-hexanediol dimethacrylate (hereinafter HDDMA), 2-hydroxyethyl acrylate and 1,3-butanediol dimethacrylate. These monomers are characterized by relatively low molecular weight (e.g., 400 or less) and low viscosity.

Other monomers may be used in combination with the foregoing co-polymerizable monomers, including viscous methacrylate-based monomers such as 2,2'-bis[4-(2-hydroxy-3-methacryloxypropoxy)phenyl]propane (hereinafter "Bis-GMA") as described in U.S. Pat. No. 3,066,112 to Bowen, which is incorporated by reference herein, or non-hydroxylated resins such as urethane dimethacrylate (hereinafter "UDMA"), or alkylated hydroxyl-containing resins such as ethoxylated bisphenol A dimethacrylate (hereinafter "EBPDMA"). EBPDMA in particular is effective in reducing the water sorption of the final product. A combination of the aforementioned resins may also be used.

The filler composition comprises bioactive particles of a bioactive glass, bioactive glass-ceramics, bioactive calcium phosphates, e.g., tricalcium phosphate, bioactive calcium apatites, e.g., hydroxylapatite, or mixtures thereof. As referred to herein, bioactive glasses are typically silicon dioxide containing compositions capable of forming hydroxyapatite when exposed to physiological fluids. Examples of bioactive glasses include those taught in U.S. Pat. Nos. 6,051,247, 4,159,358, 4,234,972, 4,103,002, 4,189,325, 4,171,544, 4,775,646, 4,851,046 and 5,074,916, all of which are incorporated herein by reference. Typical bioactive glass compositions may comprise by weight about 40 to about 90% $SiO_2$, about 4 to about 45% CaO, 0 to about 10% $Na_2O$, about 2 to about 16% $P_2O_5$, 0 to about 25% $CaF_2$, 0 to about 4% $B_2O_3$, 0 to about 8% $K_2O$ and 0 to about 5% MgO, as taught in the U.S. Pat. No. 6,171,986, which is hereby incorporated by reference. Commercially available bioactive materials useful herein include BioGlass®, PeroGlas™ and NovaBone™ materials, all available from USBiomaterials Corporation. The bioactive filler material undergoes chemical reactions at the interface between tissues and the polymerizable dental restorative material herein containing the bioactive filler material. The degradation of the macromonomers described herein allows the reaction between the tissues and the bioactive filler material to occur. The important aspect of this invention lies in the realization that the polymerizable macromonomers taught herein can be cured (as discussed below) to a sufficient hardness to support stress and strain from the forces generated during functions of the surrounding tissues, while simultaneously degrading to allow the bioactive material to interact with the surrounding tissues and regrow or repair the tissues that have been destroyed or damaged.

The bioactive filler has a particle size in the range of from about 0.5 micron to about 1000 microns, and preferably in the range of from about 1 micron to about 500 microns, and most preferably in the range of from about 2 microns to about 200 microns. The filler may be present in an amount of about 5 to 90 percent by weight of the polymerizable dental composition, and preferably in an amount of about 10 to about 80% by weight of the polymerizable dental composition, and most preferably in an amount of about 20 to about 70% by weight of the polymerizable dental composition.

The filler composition may further comprise additional inorganic calcium-containing fillers that are not bioactive. When present, the inorganic calcium-containing fillers comprise at least about 5%, preferably at least about 25%, and most preferably at least about 50% by weight of the total composition, and no more than about 90% by weight of the composition. Suitable inorganic calcium-containing fillers are particulate, having the same dimensions described above, and may be, for example, calcium hydroxide, calcium phosphates, tricalcium phosphate, calcium oxide, or mixtures comprising at least one of the foregoing inorganic calcium-containing compounds. Other nonbioactive fillers known in the art may also be present.

Other fillers which may be used in the filler composition include inorganic and organic particulates and fibrous fillers known in the art, such as particulate poly(lactide), poly (glycolide), poly(lactide-co-glycolide) or poly(methacrylate), or particulate or fibrous silica, silicate glass, quartz, barium silicate, strontium silicate, barium borosilicate, strontium borosilicate, borosilicate, lithium silicate, amorphous silica, glass fibers, alumina, zirconia, tin oxide, and titania. Particularly suitable fillers are those having a particle size from about 0.1 to about 5.0 microns, together with a fumed silica of 0.001 to about 0.07 microns and prepared by a series of milling steps comprising wet milling in an aqueous medium, surface etch milling and silanizing milling in a silane solution. Some of the aforementioned inorganic filling materials are disclosed in commonly-assigned U.S. Pat. No. 4,544,359 and No. 4,547,531 to Waknine, the pertinent portions of which are incorporated herein by reference.

It is also within the scope of the present invention that certain radiopaque/high refractive index materials, such as apatites, may be included in the filler compositions. Suitable high refractive index filler materials include, but are not limited to, high refractive index silica glass fillers. Alternatively, inert, non-toxic radiopaque materials such as barium sulfate and bismuth subcarbonate may be included. The relative amounts of additional filler and radiopaque/high refractive index materials are readily determined by those of ordinary skill in the art, depending on the particular fillers used, the intended application, the desired final properties (e.g., hardness and radiopacity), and the like.

The acrylate- or methacrylate-terminated degradable macromonomer compositions further comprise a curing composition. Suitable curing compositions for use with acrylate or methacrylate-based monomers are known in the art, and may be light cure, heat-cure, or a self cure system, or a combination thereof. Use of a dual-cure system and optional accelerators yields a composition that cures evenly and completely.

The light cure system is selected from known light-activated polymerization initiators, including but not being limited to benzil, benzoin, benzoin methyl ether, DL-camphorquinone (CQ) and benzil diketones. Either UV-activated cure or visible light-activated cure (approx. 230 to 750 nm) is acceptable. The amount of photoinitiator is selected according to the curing rate desired. A minimally catalytically effective amount is generally about 0.01% by weight of the polymeric components, and will lead to a slower cure. Faster rates of cure are achieved with amounts of catalyst in the range from greater than about 0.01% to about 5% by weight of the polymeric component.

The heat-cure initiator is selected from those known in the art such as benzoyl peroxide, lauroyl peroxide, dicumyl peroxide, 1,1'-azobis(cyclohexanecarbonitrile), or other free radical initiators. The amount of free-radical catalyst is selected according to the curing rate desired. A minimally catalytically effective amount is generally about 0.5% by weight of the polymeric components, and will lead to a slower cure. Faster rates of cure are achieved with amounts of catalyst in the range from above about 0.5% to about 6.0% by weight of the polymeric component. The heat-cure initiator is activated by the heat of reaction generated by the light-activated polymerization process. This embodiment is particularly advantageous because the composition may be supplied to the practitioner pre-mixed, that is, as a single-component mixture ready for application to the site of restoration. In a particularly preferred embodiment, the composition is supplied in pre-packaged syringes, compules, or cartridges. The compositions with a heat-cure initiator or the combination of heat and light cured initiators allow the material to be pre-cured and formed into a hardened block. Subsequent machining or CAD/CAM processing of the block to form a desired shape, such as the shape of an implant device, can then be performed. The compositions having light cure and/or self-cure initiators allow the materials to be prepared and supplied to the practitioner for application at the site of restoration. The compositions can be applied and cured either by light, or mixed, applied and self-cured. In this way, the compositions can be cured in situ, providing instant strength to the restoration.

Optional cure accelerators may further be included in the light curing composition. Polymerization accelerators are the various organic tertiary amines well known in the art. In visible light compositions, the tertiary amines are generally acrylate derivatives such as 2-(diethylamino)ethyl methacrylate (commonly known as "DEAEMA") and 2-(dimethylamino)ethyl methacrylate, in amounts in the range from about 0.1 to about 1.0 percent by weight of the polymeric composition.

Alternatively, the composition may be formulated with as a self-curing two-part system which is stored separately and mixed in equal amounts prior to use to initiate cure. Self-cure systems comprise an initiator such as a peroxide in one part, and an accelerator such as a tertiary amine, generally tertiary aromatic amines such as ethyl 4-(dimethylamino) benzoate (commonly known as "EDMAB"), 2-[4-(dimethylamino)phenyl]ethanol, N,N-dimethyl-p-toluidine (DMPT), bis(hydroxyethyl)-p-toluidine, and triethanolamine in a second part. Such accelerators are generally present in the range from about 0.5 to about 4.0% by weight of the polymeric component. Another self-curing system comprises thiourea or thiourea derivatives as the reductant and hydrogen peroxide as the oxidant, as described in U.S. Pat. No. 3,991,008. Both parts generally comprise the degradable macromonomer, co-polymerizable acrylate or methacrylate monomer, and filler in various amounts, with the initiator, for example dibenzoyl peroxide (BPO), being stored in one part, and the accelerator, e.g., N,N-dihydroxyethyl-p-toluidine being stored in another part. Equal amounts of part A and Part B are mixed by the doctor or technician immediately prior to use.

The compositions may further comprise anti-oxidants, for example BHT (2,6-di-tert-butyl-4-methylphenol) or hydroquinone methyl ether in amounts in the range from about 0.1 to about 0.3% by weight of the polymerizable components; ultraviolet stabilizers to prevent discoloration, for example benzophenones such as 2-hydroxy-4-methoxybenzophenone, benzotriazoles, such as 2-(2'-hydroxy-5'-methylphenyl) benzotriazole, 2-(2-hydroxy-5-tert-octylphenyl) benzotriazole (available under the trade name UV-54 from American Cyanamid Company) and other derivatives thereof; fluorescent whitening agents such as 2,5-bis(5-tert-butyl-2-benzoxazole) thiophene (available under the trade name UV-OB); trace amounts of FDA and FDC approved dyes, for example iron oxides, yellow No. 5, yellow No. 6, and the like; and other additives known in the art.

Medicaments may also be included in the compositions in an amount effective to prevent infection and/or inflammation, generally from about 1% to about 10% by weight of the total composition. Suitable medicaments include but are not limited to pain relieving agents such as Novocaine (procaine hydrochloride), Benzocain (ethyl aminobenzoate), ascorbic acid, butacaine sulfonate, dibutacaine hydrochloride, antibiotics such as sulfadiazine, procaine penicillin, aureomycin, streptomycin, terramycin, chloramphenicol, butabarbital, diethyl stilbestrol, and anti-inflammation agents such as p-aminosalicylic acid, aspirin, and the like.

In one embodiment, a method of restoring a tooth comprises preparing a site on a tooth to be restored; and applying a composition comprising (a) at least one degradable macromonomer having terminal acrylate or methacrylate groups; (b) a curing composition; (c) a filler composition comprising bioactive particles; and (d) optionally one or more co-polymerizable acrylate or methacrylate monomers. Preferably, the site to be restored is a root canal.

Another preferred embodiment of the present invention is a method of repairing a bone comprising preparing a site to be restored in a portion of a bone; and applying a composition comprising (a) at least one degradable macromonomer having terminal acrylate or methacrylate groups; (b) a curing composition; (c) a filler composition comprising bioactive particles; and (d) optionally one or more co-polymerizable acrylate or methacrylate monomers.

The present invention is preferable to the currently available art for root canal sealants, implant materials, bone cements, and pulp capping compositions because the compositions of the present invention are expected to be non-toxic, biodegradable and biocompatible. These properties are ideal for tissue regrowth in the surrounding tissue and dentine when the compositions are used in pulp capping procedures or root canal procedures. Also, the present compositions have low shrinkage, which is required for use as root canal sealants.

The invention is further illustrated by the following non-limiting Examples. Synthesis of PLAMA was in accordance with Huang (1996).

EXAMPLE 1

Degradation of Cured PLAMA/TEGDMA Compositions

The degradation of cured PLAMA/TEGDMA for varying quantities of PLAMA was studied in a buffer solution of pH 7 over time. The curing of PLAMA/TEGDMA was performed in a light box for 2 minutes using a curing composition comprising 0.2% by weight CQ and 0.2% by weight DEAEMA. PLAMA and TEGDMA were mixed to give various weight percents (based on the total resin composition) of PLAMA in accordance with Table 1 below. The amount of TEGDMA or other suitable crosslinker/diluent resin can also be varied according to the viscosity and molecular weight of the PLAMA used. The samples were prepared as 1 mm thick disks, weighed to determine the original weight, and immersed in pH 7 buffer and then stored at 37° C. The samples were removed from the solution monthly, oven-dried, and weighed to determine degradation, as reflected by weight loss. Weight loss is calculated by subtracting the dried weight from the original weight, and dividing that amount by the original weight. Results are shown in Table 1.

TABLE 1

| PLAMA (wt. %) | Weight Loss (wt. %) | | | |
|---|---|---|---|---|
| | 0.5 month | 1 month | 2 month | 3 month |
| 25 | 4.2 | 10.8 | 21 | 24 |
| 50 | 3.9 | 23.0 | 29 | 31 |
| 55 | 6.8 | 23.5 | 34 | 35 |
| 60 | 5.0 | 29.0 | 44 | 46 |
| 75 | 11.5 | 41.0 | 56 | 59 |
| 90 | 17.7 | 56.0 | 69 | 73 |
| Control* | −0.05 | −0.04 | 0.01 | 0.02 |

*BIS GMA/UDMA/HDDMA (33/34/33) resin by weight with 0% PLAMA

As shown in Table 1, degradation of the samples is related to the weight percent of PLAMA used to prepare the samples, such that degradation of the samples increases with the increasing quantities of PLAMA relative to TEGMA. When no PLAMA is present, no degradation is observed.

EXAMPLE 2

Shrinkage of Copolymerized PLAMA/TEGDMA

Shrinkage of PLAMA/TEGDMA resins was measured by a dilatometer (ADA Health Foundation, Maryland, USA). The measurement was performed on samples prepared by mixing 20 vol % of fumed silica (OX-50 from Degussa) into resins copolymerized using varying quantities of PLAMA. Results are shown in Table 2.

TABLE 2

| PLAMA (wt. %) | Shrinkage (% by volume) |
|---|---|
| 60 | 5.59 |
| 75 | 3.94 |
| 90 | 2.92 |
| Control* | 6.14 |

*BIS GMA/UDMA/HDDMA (33/34/33) resin by weight

Shrinkage is also related to weight percent of PLAMA present, such that the higher the ratio of PLAMA used, the lower the shrinkage observed. Lower shrinkage is essential in root canal sealing materials.

EXAMPLE 3

Self-Cure of PLAMA/TEGDMA Resins

Self-curing formulations of 70/30 by weight PLAMA/TEGDMA compositions comprising organic and/or inorganic fillers were studied, using a two-part formulation. The inorganic fillers are $BaSO_4$ and tricalcium phosphate (TCP). An exemplary formula is shown in Table 3. When equal parts of the base and catalyst formulation are mixed, this formula has a viscosity suitable for root canal sealants and for pulp capping.

TABLE 3

Exemplary Formula of Self-Cured PLAMA/TEGDMA

| Component | PLAMA/TEGDMA (70/30 by wt.) | $BaSO_4$ | TCP | BHT | DMPT | BPO |
|---|---|---|---|---|---|---|
| Base | 60 g | 20 g | 20 g | 300 ppm | 1 g | — |
| Catalyst | 60 g | 20 g | 20 g | 600 ppm | — | 2 g |

Gel time = 7 min, 30 sec.
Setting time = 10 min, 20 sec.

EXAMPLE 4

Degradation of Example 3

Example 3 above was tested for degradation using the method of Example 1. Results are shown in Table 4.

TABLE 4

| Time (month) | 0.5 | 1 | 2 | 3 |
|---|---|---|---|---|
| Degradation (wt. %) | 6.4 | 13 | 22 | 26.4 |

EXAMPLE 5

2-(Caprolactone)ethyl methacrylate (CLMA) was used as the base resin. PGLMA/HDDMA in the ratio of 70/30 was used as the catalyst resin. An exemplary formula is shown in Table 5. When equal parts of the base and catalyst formulation are mixed, this formula has a viscosity suitable for root canal sealants and for pulp capping.

TABLE 5

| Component | CLMA PLGMA/ HDDMA | $BaSO_4$ | TCP | $Ca(OH)_2$ | BHT | BPO | DMPT |
|---|---|---|---|---|---|---|---|
| Base | 50 g | 20 g | 20 g | 10 g | 0.025 g | — | 0.75 g |
| Catalyst | 60 g | 20 g | 20 g | — | 0.60 g | 1.8 g | — |

Gel time = 12 min, 30 sec.
Setting time = 16 min.

EXAMPLE 6

Degradation of Example 5

Example 5 was tested for degradation using the method of Example 1. Results are shown in Table 6.

TABLE 6

| Time (day) | 7 | 15 | 21 | 30 |
|---|---|---|---|---|
| Degradation (wt. %) | 3.7 | 4.4 | 5.1 | 6.4 |

For regular non-degradable cement (Cement C&B, Jeneric/Pentron), the weight loss in a month is about 0.3%.

EXAMPLE 7

The monomers used in this formulation are 70/30 PLAMA/TEGMA.

TABLE 7

| Component | 70/30 PLAMA/ TEGMA | $BaSO_4$ | TCP | BHT | Acetyl thiourea | Cumene hydroperoxide |
|---|---|---|---|---|---|---|
| Base | 60 g | 20 g | 20 g | 0.06 g | 4 g | — |
| Catalyst | 60 g | 20 g | 20 g | 0.06 g | — | 4 g |

Gel time = 7 min, 45 sec.
Setting time = 11 min, 45 sec.

EXAMPLE 8

100 grams of PLAMA with an additional 0.2 parts CQ and 0.2 parts DEAMA were mixed. The resin composition was prepared as 1 mm thick disc and cured for 2 minutes in a light box, giving a hardened solid. This composition may be used as a degradable surface sealant.

EXAMPLE 9

Physical Properties of Dual Curable Paste-Paste Two-Part Compositions

Paste-paste formulations containing Bioglass filler were evaluated for flexural strength and weight loss. The following Table 8 shows base and catalyst components for two-part compositions.

TABLE 8

| | Composition | | | |
|---|---|---|---|---|
| Ingredients | Base 1 | Base 2 | Catalyst 1 | Catalyst 2 |
| PLAMA | | | 17.5 | |
| PEGDMA | 17.5 | 17.5 | 17.5 | 17.5 |
| UDMA | 17.5 | 17.5 | | 17.5 |
| BHT | 0.05 | 0.05 | 0.05 | 0.05 |
| DHEPT | 0.35 | 0.35 | | |
| BPO | | | 0.85 | 0.85 |
| Camphorquinone | 0.05 | 0.05 | | |
| EDMAB | 0.10 | 0.10 | | |
| Bioglass | 20 | | | |
| Tricalcium Phosphate | | | 10 | 10 |
| Barium Sulfate | 44.45 | 44.45 | 44.1 | 44.1 |
| Silane treated Barium Glass | | 20 | 10 | 10 |

The base and catalysts set forth in Table 8 were mixed in ratios of 1:1 by volume, which was performed by using a dual-barrel cartridge with an auto-mixing tip. The base and catalyst were preloaded into each side of a dual-barrel cartridge, such as that used for Cement-It® Universal C & B luting cement cartridge, available from Pentron Corporation. As shown in Table 8, Base 1 contains Bioglass and Catalyst 1 contains PLAMA. Base 1 was mixed with Catalyst 1 as the preferred composition. Base 1 was also mixed with Catalyst 2. Base 2 was mixed with Catalyst 1 and Base 2 was mixed with Catalyst 2. The mixtures were then self-cured and hardened after about 10 minutes and flexural strength was measured after 24 hours in a dry state at room temperature and in following conditions and schedule. Flexural strength was measured for various samples after immersion in water for 24 hours, 48 hours, 168 hours and 720 hours. Weight loss was measured on all of the samples at the end of 720 hours in water. The following Table 9 lists the flexural strength and weight loss of the two-component compositions.

TABLE 9

| Properties | Base 1 + Catalyst 1 | Base 1 + Catalyst 2 | Base 2 + Catalyst 1 | Base 2 + Catalyst 2 |
|---|---|---|---|---|
| Flexural strength* (S.D.) for samples kept dry for 24 hours at room temperature | 4735 psi (200) | 9555 psi (963) | 9655 psi (518) | 8728 psi (762) |
| Flexural strength* (S.D.) for samples kept in $H_2O$ for 24 hours at 37° C. | 1456 psi (122) | 6266 psi (152) | | |
| Flexural strength* (S.D.) for samples kept for two days in $H_2O$ at 37° C. | | | 6930 psi (1114) | 9161 psi (588) |
| Flexural strength* (S.D.) for samples kept for seven days in $H_2O$ at 37° C. | 1446 psi (174) | 3710 psi (268) | | |
| Flexural strength* (S.D.) for samples kept for 30 days in $H_2O$ at 37° C. | 1098 psi (173) | 3641 psi (270) | 4800 psi (351) | 8902 psi (563) |
| Weight loss** measured after samples kept for seven days in $H_2O$ at 37° C. | 4.1% | 2.5% | 2.2% | 0.9% |

*The sampling and the testing methods of the flexural strength were conducted according to ISO Specification 4049:2000 (B) except for the aging conditions as specified.
**The weight loss measurement was performed based on the solubility test of ISO specification 4049:2000 (E), except the results herein are expressed as percentage weight loss.

As set forth in Table 9, the combination of Base 1 (containing Bioglass filler) and Catalyst 1 (containing PLAMA) shows the most degradation after seven days in water. Weight loss is also greatest for the Base 1/Catalyst 1 combination. These properties are ideal for tissue regrowth in the surrounding tissue and dentine when the composition is used in pulp capping procedures or root canal procedures. The combination of Base 1 (containing Bioglass) with Catalyst 2 also provided good degradation properties. The combination of Base 2 with Catalyst 1 (containing PLAMA) provided the third best degradation properties. The combination of Base 2 with Catalyst 2 provides very little degradation.

The results indicate that the presence of PLAMA in combination with Bioglass show the most degradation and weight loss. The presence of Bioglass without PLAMA shows very good degradation and the presence of PLAMA shows very good degradation. Accordingly, the combination of a degradable macromonomer and a bioactive filler provide optimum degradation properties beneficial to tissue regrowth.

EXAMPLE 10

Physical Properties of Powder-Liquid Two-Part Compositions

Powder-liquid formulations containing PLAMA and Bioglass filler were evaluated for flexural strength and weight loss. The following Table 10 shows liquid and powder compositions for the two-part compositions.

TABLE 10

| Ingredients | Liquid A (by weight %) | Liquid B (by weight %) | Powder Composition (by weight %) |
|---|---|---|---|
| PLAMA | 99.5 | | |
| UDMA | | 99.5 | |
| DMPT | 0.5 | 0.5 | |
| BPO | | | 1.5 |
| Bioglass* | | | 98.5 |

*The bioactive glass used herein has particle sizes of less than about 200 μms and an approximate composition of about 45% $SiO_2$, about 24.5% $Na_2O$, about 24.5% CaO and about 6% $P_2O_5$ by weight as taught in U.S. Pat. No. 4,171,544, which is hereby incorporated by reference.

The liquid and powders were mixed in ratios of about 1:1 by weight on a glass pad with a dental spatula. The mixtures were then self-cured in about five minutes and flexural strengths were measured under dry conditions and after the samples were immersed in water for 24 hours and 168 hours. Weight loss was measured at the end of the 168 hour period. The following Table 11 lists the flexural strength and weight loss of the two-component compositions.

TABLE 11

| | Tested properties | |
|---|---|---|
| (tested under following conditions) | Combination of Liquid A + Powder (Mixed in about 1:1 by weight) | Combination of Liquid B + Powder (Mixed in about 1:1 by weight) |
| Flexural Strength (S.D.) tested approximately 30 minutes after material has set | 3538 psi (457) | 3750 psi (384) |

TABLE 11-continued

| (tested under following conditions) | Tested properties | |
|---|---|---|
| | Combination of Liquid A + Powder (Mixed in about 1:1 by weight) | Combination of Liquid B + Powder (Mixed in about 1:1 by weight) |
| Flexural Strength (S.D.) tested on samples kept dry for one day at room temperature | 4058 psi (329) | 5062 psi (592) |
| Flexural Strength (S.D.) tested on samples submerged in $H_2O$ at 37° C. for one day | 410 psi (74) | 3802 psi (427) |
| Flexural Strength (S.D.) tested on samples submerged in $H_2O$ at 37° C. for one week | 354 psi (104) | 3302 psi (266) |
| Weight Loss Measurement ($\mu g/mm^3$) on samples submerged in $H_2O$ at 37° C. for one week | 158 (12.7) | 46.7 (2.8) |

The results have shown again that the combination of the degradable macromonomer and bioactive fillers is superior in the degradation process to the non-degradable polymer-based composition, even though the composition may contain some bioactive fillers.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method of forming a dental or medical restoration comprising:
    preparing a site to be restored in a tooth or bone; and applying a composition comprising
    (a) at least one degradable macromonomer having terminal acrylate or methacrylate groups and consisting essentially of the reaction product of lactide, glycolide, or a mixture thereof in the presence of a compound having at least one active hydrogen and at least one acrylate or methacrylate functionality;
    (b) a curing composition;
    (c) a filler composition comprising bioactive particles of bioactive glass, bioactive glass-ceramics, bioactive calcium phosphates, bioactive calcium apatites, or mixtures thereof; and
    (d) optionally one or more co-polymerizable acrylate or methacrylate monomers; and curing the compositions.

2. The method of claim 1, wherein the active hydrogen is a hydroxyl hydrogen.

3. The method of claim 1, wherein the compound is selected from the group consisting of hydroxyalkyl acrylates and methacrylates wherein the alkyl group has from 1 to 12 carbons, and mixtures thereof.

4. The method of claim 3, wherein the compound is selected from the group consisting of 2-hydroxyethyl methacrylate, 2-hydroxyethyl acrylate, diethylene glycol monomethacrylate, diethylene glycol monoacrylate, hydroxypropyl methacrylate, hydroxypropyl acrylate, tetraethyleneglycol monomethacrylate, tetraethyleneglycol monoacrylate, pentaethyleneglycol methacrylate, hydroxypolyethyl methacrylate, pentaethyleneglycol monoacrylate, dipropyleneglycol monomethacrylate, dipropyleneglycol monoacrylate, phenoxyhydroxyphenyl methacrylate, and mixtures thereof.

5. A method of forming a dental or medical restoration comprising:
    preparing a site to be restored in a tooth or bone; and applying a composition comprising
    (a) 2-(polycaprolactone)ethyl methacrylate;
    (b) a curing composition;
    (c) a filler composition comprising bioactive particles of bioactive glass, bioactive glass-ceramics, bioactive calcium phosphates, bioactive calcium apatites, or mixtures thereof; and
    (d) optionally one or more co-polymerizable acrylate or methacrylate monomers; and curing the compositions.

6. The method of claim 1, wherein the co-polymerizable acrylate or methacrylate monomer is a diluent monomer present in an amount effective to provide delivery to the restoration site using an applicator.

7. The method of claim 6, wherein the diluent monomer is selected from the group consisting of liquid dimethacrylate, trimethacrylate, glycerol dimethacrylate, ethylene glycol dimethacrylate, tri(ethylene glycol) dimethacrylate, tetra(methylene glycol) dimethacrylate, polyethylene glycol dimethacrylate, trimethylolpropane trimethacrylate, 1,6-hexanediol dimethacrylate, 2-hydroxyethyl acrylate, and 1,3-butanediol dimethacrylate.

8. The method of claim 1, wherein the curing composition is selected from the group consisting of light-activated polymerization initiators, heat-cure initiators, a self-curing two-part system, and combinations thereof.

9. The method of claim 1, wherein the curing composition is a self-curing two-part system mixed prior to use comprising an initiator in one part and an accelerator in a second part whereby the two parts contain equal or various amounts of the degradable macromonomer and co-polymerizable acrylate or methacrylate monomer.

10. The method of claim 1, wherein the filler composition further comprises non-bioactive particles comprising inorganic calcium compounds, calcium phosphates, calcium hydroxide, calcium oxide, tricalcium phosphate, poly(lactide), poly(glycolide), poly(lactide-co-glycolide), poly(methacrylate), silica, fumed silica, silicate glass, glass fibers, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania and combinations thereof.

11. The method of claim 1, wherein the degradable macromonomer having terminal acrylate or methacrylate groups is poly(lactide-2-hydroxyethyl methacrylate) (PLAMA).

12. The method of claim 1, wherein the degradable macromonomer having terminal acrylate or methacrylate groups is poly(glycolide-hydroxy ethyl methacrylate).

13. The method of claim 1, wherein the degradable macromonomer having terminal acrylate or methacrylate groups is poly(lactide glycolide-hydroxy ethyl methacrylate) (PGLMA).

* * * * *